United States Patent
Denney et al.

(10) Patent No.: US 7,489,972 B2
(45) Date of Patent: Feb. 10, 2009

(54) METHOD OF DETECTING WHEN ELECTRODE PADS HAVE BEEN HANDLED OR REMOVED FROM THEIR PACKAGE

(75) Inventors: Douglas Denney, Sammamish, WA (US); Thomas Lyster, Bothell, WA (US); Joseph Diederichs, Seattle, WA (US); Daniel Kingsbury, Seattle, WA (US); Eric Jonsen, Seattle, WA (US); Alan Greenstein, Seattle, WA (US); Thomas A. Solosko, Issaquah, WA (US); Daniel J. Powers, Issaquah, WA (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 310 days.

(21) Appl. No.: 10/561,335

(22) PCT Filed: Jun. 1, 2004

(86) PCT No.: PCT/IB2004/001937

§ 371 (c)(1),
(2), (4) Date: Dec. 15, 2005

(87) PCT Pub. No.: WO2005/000392

PCT Pub. Date: Jan. 6, 2005

(65) Prior Publication Data

US 2006/0142810 A1 Jun. 29, 2006

Related U.S. Application Data

(60) Provisional application No. 60/483,197, filed on Jun. 27, 2003.

(51) Int. Cl.
*A61N 1/00* (2006.01)
(52) U.S. Cl. .................................... 607/142
(58) Field of Classification Search ............... 607/4–6, 607/142; 600/392
See application file for complete search history.

(56) References Cited

U.S. PATENT DOCUMENTS

| 3,805,795 | A | * | 4/1974 | Denniston et al. ............. 607/6 |
| 4,706,680 | A | * | 11/1987 | Keusch et al. ............... 600/392 |
| 5,645,571 | A |   | 7/1997 | Gilman et al. |
| 5,700,281 | A |   | 12/1997 | Stolte et al. |
| 6,075,369 | A |   | 6/2000 | Morgan |
| 6,125,299 | A | * | 9/2000 | Groenke et al. ............... 607/6 |
| 2003/0055478 | A1 |   | 3/2003 | Griesser et al. |

\* cited by examiner

*Primary Examiner*—George Manuel
(74) *Attorney, Agent, or Firm*—Tony Piotrowski

(57) ABSTRACT

Handling or removal of a pair of pre-connected defibrillator electrode pads from their package, or a compartment in the defibrillator, is detected in order to effectively time the issuance of prompts to guide the user. Detection occurs when an impedance level between the electrode pads varies sufficiently over time to indicate occurrence of the handling or removal event. The pads are preferably configured to leverage variability in the impedance that results from bending of pads during handling or removal.

12 Claims, 5 Drawing Sheets

METHOD OF DETECTING WHEN ELECTRODE PADS HAVE BEEN HANDLED OR REMOVED FROM THEIR PACKAGE

CROSS REFERENCE TO RELATED APPLICATION

This application claims the benefit of U.S. provisional application Ser. No. 60/483,197 filed Jun. 27, 2003, which is incorporated herein.

BACKGROUND OF THE INVENTION

1. Field of the Invention

The present invention relates to electrodes, and, more particularly, to monitoring electrodes.

2. Discussion of the Prior Art

In the US alone, over 350,000 people die annually from Sudden Cardiac Arrest. Many of these victims have no prior warning of heart disease, and 70% die outside the hospital. The only treatment for an SCA victim is to provide an immediate, high-energy electric shock through the heart. Minimizing the time to first shock is critical since, for every minute after 4 minutes, the chances of resuscitation decrease by 10%. If a shock is not applied within 10 minutes, the chances of resuscitation are almost zero.

U.S. Pat. No. 5,700,281, issued on Dec. 23, 1997, hereinafter "the '281 patent," the entire disclosure of which is incorporated herein by reference, discloses the use of prompts to guide a user in assisting an SCA victim. The '281 patent uses impedance values between the electrode pads to determine the stage of a rescue attempt in order to prompt and thereby guide the user. Yet, guidance for the deployment and application of the electrode pads, in a timely manner is not available.

SUMMARY OF THE INVENTION

In an effort to save as many as possible of the 350,000 lives per year lost to SCA, Automated External Defibrillators, or AEDs, are being placed where people live, work, travel and play. The objective is to provide the tool that can be used by a minimally trained or untrained witness to administer these lifesaving shocks as quickly as possible.

Because the witnesses are not usually trained in the use of defibrillators, AEDs must not only interpret the heart rhythm to determine if a shock is required, but they must also guide the users through the process of calling Emergency Medical Systems, removing the clothes from the patient's chest, removing the pads from their sealed package, and applying these pads to the correct location on the patient's chest. Different users complete these steps at different paces. For example, removing the clothes to bare the patient's chest might be a quick process if the patient is only wearing a tee-shirt, but will take much longer if there are multiple layers that need removing or cutting away.

In order to minimize confusion during an already anxious event, the AED should not begin to give the voice prompts for the next action, like applying the pads to the patient's bare chest, until the current action, i.e. removing the clothes, has been completed. The challenge lies in how the AED detects when the current action has been completed.

Some AEDs require the user to press a button when the current action has been completed. This is a clean method of advancing the prompts, but breaks down if the user fails to press the button. If the button is not pressed, the voice prompts do not proceed and precious time is lost while the user tries to determine the cause of the delay.

Some AEDs include only minimal, more generalized prompts, which do not need to be advanced. However, these prompts do not guide the user step-by-step through the process, and may not be sufficient to help a confused user. Again, precious time may be lost.

Some AEDs may advance their prompts after a certain amount of time, regardless of whether the user has completed the current action or not. This can create confusion and anxiety for the user if the current step has not yet been completed, or if the current step is completed quickly.

Advantageously, the present invention provides a solution to accurately advance the voice prompts between two very critical actions: removing the clothes from the patient's chest and applying the pads to the patient's chest. In a preferred method of the invention, the pad-to-pad impedance of pre-connected electrode pads is continuously monitored from the moment the AED has been turned on, or from a certain time after the device has been turned on, watching for changes or variability in this impedance measurement.

Pre-connected electrode pads are pads that have been electrically attached to the defibrillator prior to the moment of need. In this way, the pads are ready for immediate deployment. In addition, if these pre-connected pads are electrically connected to each other, the AED can measure the impedance between the pads.

A high-impedance pad-to-pad connection is described in pending, commonly-owned US Patent Publication 2003/0055478, entitled "Medical Electrode and Release Liner Configuration Facilitating Packaged Electrode Characterization," filed on Sep. 14, 2001, hereinafter "the '478 publication," the entire disclosure of which is incorporated herein by reference.

The pad-to-pad impedance level is fairly constant while the pre-connected pads are sealed untouched inside their package which hereinafter is intended to refer to any type of container, such as a rigid sealed tray or a flexible sealed film package, or combination of both. However, when a user opens the pads' package and pulls out the pads, the pad-to-pad impedance changes due to the physical manipulation, handling and bending of the pads. If the magnitudes of these impedance changes are great enough, over the existing noise floor, the AED will detect them and determine that the pads state is being changed: from being sealed in their package to being handled or removed from their package.

As mentioned previously, correct and timely pad placement is essential to the efficacy of the shock. By sensing that the pads are being physically handled and manipulated by the user, the AED can determine that the previous action of calling 911 and removing the clothes has been completed. In this way, with no further button presses required of the user, the AED will immediately cease repeating its "Remove all clothes from the patient's chest" prompt and begin repeating the new prompt, "Look carefully at the pictures on the first pad. Remove the pad from the release liner and apply it exactly as shown in the picture." This invention allows the AED to advance to the next prompt when, and only when, the user is ready to progress to the next step, without additional input from the user.

BRIEF DESCRIPTION OF THE DRAWINGS

Details of the invention disclosed herein shall be described with the aid of the figures listed below, wherein like features are numbered identically throughout the several views.

DETAILED DESCRIPTION OF THE PREFERRED EMBODIMENTS

Figure 1:
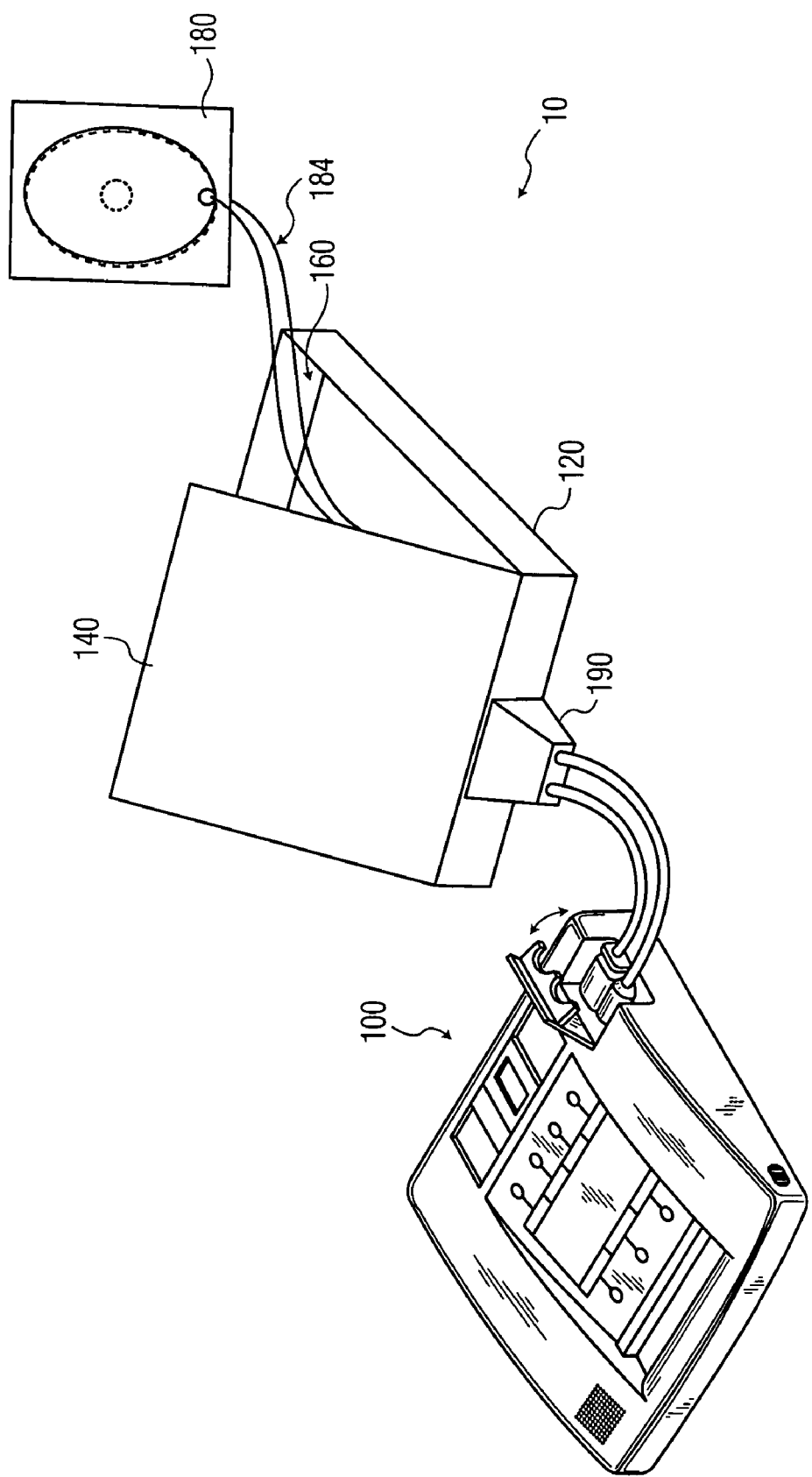
FIG. 1 is a perspective view of a defibrillation system according to the present invention.

FIG. 1 portrays an exemplary defibrillation system 10 of the present invention including a defibrillator 100 and a rigid cartridge 120 having a lid 140 shown in the open position. The cartridge 120 further has, defined in part by the lid 140, an electrode compartment 160 in which a pair of electrode pads 180 (the second pad being obscured by the visible one) may be stored. Each pad 180 is attached in electrical connection by a lead wire 184 to an electrical interface 190 which in turn connects to the defibrillator 100 or other medical device.

Figure 2:
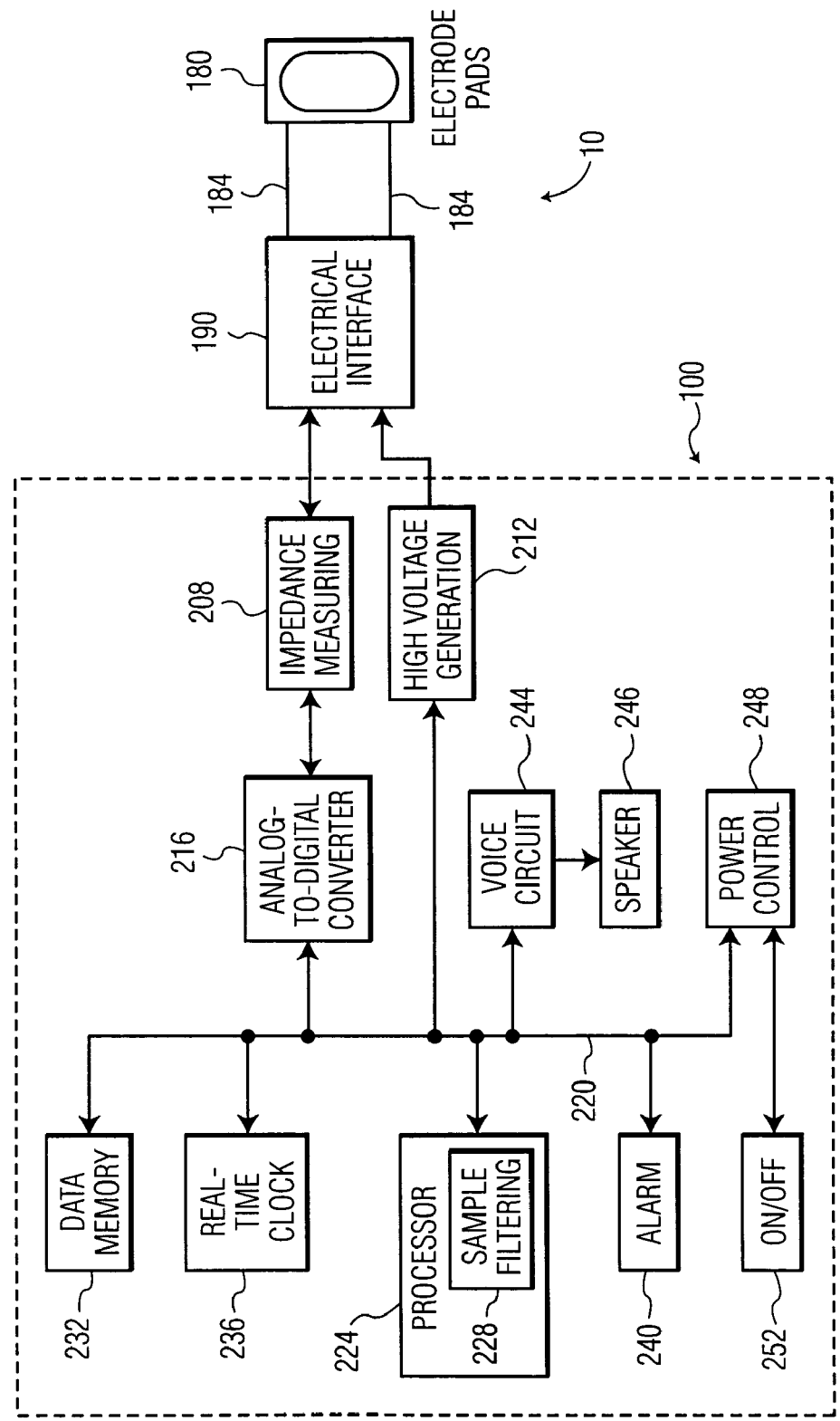
FIG. 2 is a functional block diagram of components within the defibrillator according to the present invention and depicted in FIG. 1.

FIG. 2 is a simplified block diagram showing functional components of the defibrillation system 10 in accordance with the invention. The electrode pads 180 are connected by means of the respective lead wires 184 and the electrical interface 190 to an impedance measuring module 208 and to a high voltage generation module 212, both within the defibrillator 100 (indicated by the broken line). Although the module 208 is portrayed as an impedance measuring module, module 208 can more generally operate to measure other electrical characteristics of an electric circuit, e.g. resistance or reactance. The impedance measuring module 208 is connected by an analog-to-digital converter 216 to a data and control bus 220, to which the high voltage generation module 212 is connected directly. On the bus 220 is a processor 224 having a sample filtering module 228, a data memory module 232, a real-time clock 236, an alarm 240, a voice circuit 244 and a power control module 248. The voice circuit 244 drives a speaker, and the power control module 248 is actuated on/off by an on/off switch 252.

The defibrillator 100 periodically samples an impedance magnitude, filters the samples and detects variation over time in the magnitude, to determine that the electrode pad 180 has been handled or removed. Based upon such a determination, it can safely be presumed that the user has advanced to the stage where the victim has been prepared for defibrillation, e.g. the victims clothing has been removed. The event of an electrode being handled is intended, for purposes of this disclosure, to include the case of handling an electrode indirectly, e.g. while it is encased within a flexible package As a further inventive feature, the electrode pad 180 of the present invention is configured with a high impedance path, such as that described in connection with FIG. 14B of the '478 publication. Advantageously, voltage changes induced by variations in impedance are more pronounced, and therefore more easily detected, for an electrical path through a high impedance circuit. Additionally, the high impedance allows the defibrillator 100 to easily determine when the electrode pad has been applied to a patient in which case the measured impedance is markedly lower. An impedance level of 400 ohms, for example, is sufficiently high to indicate that the pads 180 are not being applied to a patient.

In operation, the impedance measuring module 208 receives a clock signal having a predetermined magnitude from clock 236, and applies the signal to the electrode pad 180 by means of the electrical interface 190. Electric current representative of the clock signal travels a path through electrodes of electrode pads 180 by means of an electrically conductive medium between the electrodes. The magnitude of the clock signal received back from electrode pad pair 180 through connector 204 is monitored by impedance measuring module 208. An impedance signal representative of the impedance present across AED connection 204 is then generated by module 208 as a function of the ratio of the magnitudes of the applied and received clock signals (i.e., the attenuation of the applied signal). The impedance signal representative of the impedance measured by module 208 is digitized by A/D converter 216 to produce samples. The samples are either stored in the data memory 232 for retrieval and subsequent processing by processor 224 or are provided directly to processor 224. Each sample is filtered by the sample filtering module 228. From the filtered samples, the processor 228 detects variation over time in the impedance magnitude, indicating the handling or removal of the electrode pad 180. User prompts may be presented over the speaker 248. Alternatively, or in addition, viewable screens or indicators provided on the housing 120 may display prompts. The configuration depicted in FIG. 2 represents one example of how the invention maybe implemented as is not intended to be limitative of the scope of the invention.

In a preferred embodiment, for example, defibrillator components shown in FIG. 27 of the '478 publication perform or are readily adapted to perform the above functions as would be clear to those of ordinary skill in the art. For example, as shown in FIG. 27 and described in the accompanying text, the status measurement unit 2760, and possibly an appropriate combination of the memory 2730, the data card 2736, the processing unit 2732, the first gate array 2720, the second gate array 2722 and/or the temperature sensor 2770 may be implemented to assist in or manage the impedance calculations of the present invention.

Figure 3:
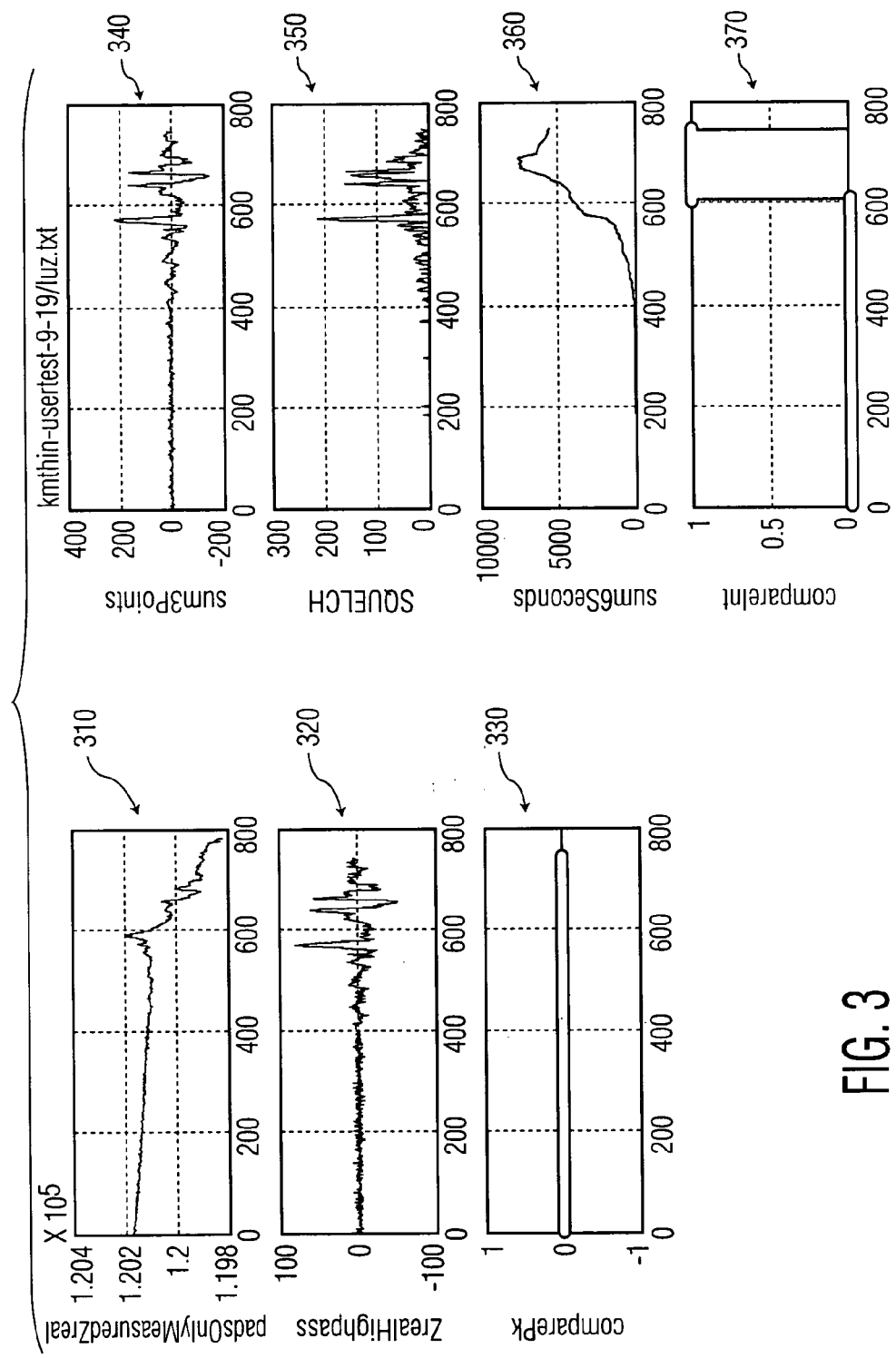
FIG. 3 is progressive series of waveforms representative of corresponding stages in the processing of pad-to-pad impedance values according to the present invention.

FIG. 3 illustrates waveforms that track the state of the electrode pads 180, showing at which point it is determined that the pads are being handled or removed from their package. The waveforms, graph-to-graph, are representative of progressive processing stages in the processing of impedance signals sampled in accordance with embodiments of the present invention. This multi-stage processing is directed to detecting disturbance in pad-to-pad impedance levels that is significant after accounting for noise, such as measurement noise in the base signal level. These methods for detecting significant impedance variation are merely exemplary and not limitative of the intended scope of the present invention.

In the following seven graphs, the units of the vertical axis are not in ohms, but in counts. Each count equates to a percentage of an ohm. The horizontal axis shows the data points, as explained in more detail below.

The first graph 310, labeled, "padsOnlyMeasuredZreal," is the product of five steps:
1) Sampling the 32 bit ASIC real-impedance pad-to-pad data at 200 samples/second.
2) Rounding each data sample from 32 bits to 16 bits.
3) Forming, for each sample, a window of length 5, i.e., including two consecutive samples on each side, and substituting for the sample the median of the 5 values.
4) Summing 10 consecutive medians produced in step 3) and dividing the sum by 10 to produce a single sample. The sample rate is now 20 data samples/second.
5) Subtracting the constant hardware impedance, e.g. 40 ohms.

The second graph 320, labeled "ZrealHighpass," shows the results after a subsequent high pass filtering step. In this step, the average of 2 seconds worth of data, centered around each data point, is subtracted from each data point. This eliminates the nominal pad-to-pad impedance level and any existing impedance trends (like the downward slope shown in the first graph), and shows only immediate impedance variations around the undisturbed level. The graph presented here clearly shows the period when the pads were sitting quietly in their package and then large impedance variations when the pads 180 were being handled. A variation over time in the magnitude of the impedance allowed the event of the pads 180 being handled to be detected.

The third graph 330, labeled "comparePk," is the Boolean result (0 or 1) of the comparison of each ZrealHighpass point to a predetermined single-peak threshold. If two points in a row exceed the single-peak threshold, the corresponding point in "comparePk" goes from 0 to 1 indicating to the device that the pads have been handled. In this example, no points exceeded the single-peak threshold. As a result, "comparePk" remained at 0.

Without mechanical enhancement, it is unlikely that a single point will exceed the single-peak threshold when the pads are being handled gently. Therefore, further processing is required which integrates the signals over several seconds to determine if a series of smaller impedance variations are significant, indicating that a user is handling the pads.

The fourth graph 340, labeled "sum3Points," is the result of a low-pass filtering step that has been applied after the high-pass filtering step and shows the moving sum of every three points. This processing step increases the magnitude of the large impedance variations, and smoothes many of the small magnitude variations.

The fifth graph 350, labeled "squelch," shows the result of taking the absolute value of each point of the data points in "sum3Points" and applying the squelching function to them. This function reduces the values of all data points below the predetermined squelch threshold to zero. Since small impedance variations are assumed to be noise in the measurement, reducing them to zero eliminates the effect of noise upon the following integration steps.

The sixth graph 360, labeled "sum6Seconds," shows the moving 6-second sum of all the data points shown in "squelch." This is the integration or sum of all the non-noise pad-to-pad impedance variations occurring during each rolling 6-second interval or time window. If the sum of any rolling 6-second interval exceeds a predefined threshold, then the Boolean result in the final chart 370, "compareInt," changes from 0 to 1 indicating to the device that enough pads handling has been detected to determine that the pads are being removed from their package. Specific embodiments of the AED 100 and the electrode pads 180 may enhance the ability to distinguish the event of removing the pads from the event of merely handling the pads, as will be further described below. Also, the size of the rolling interval is not limited to 6 seconds, but more generally may be any length. A larger interval is more sensitive to pad disturbance, but generally slows the advance of user prompts and is more prone to false triggering. Similarly, a shorter interval generally quickens the advance of user prompts and is less prone to false triggering, but is more likely to miss detecting some pad handling/removal events.

In this example, the last chart 370 showed that the sum6Seconds exceeded the threshold just after data point #600. When this occurred, the value in "compareInt" changed from 0 to 1, indicating that the pads had been handled.

One note about this integration step—in the preferred embodiment, the 6-second rolling integration in calculating the moving sum starts from the moment the device is turned on through user actuation of the switch 252. In this way, the first 6 seconds are long past by the time the user reaches for the pads, and the user does not have to wait several seconds for the device to detect pads removal. Alternatively, the calculation can commence a predetermined time period after switch actuation.

As a safety catch, one additional embodiment of this invention is to include a time-based prompt advancement along with the impedance variability detection. In this way, if after a certain predetermined time, the user has not begun to remove the pads from their package, the AED 100 will automatically advance to the next voice prompt.

Figure 4:
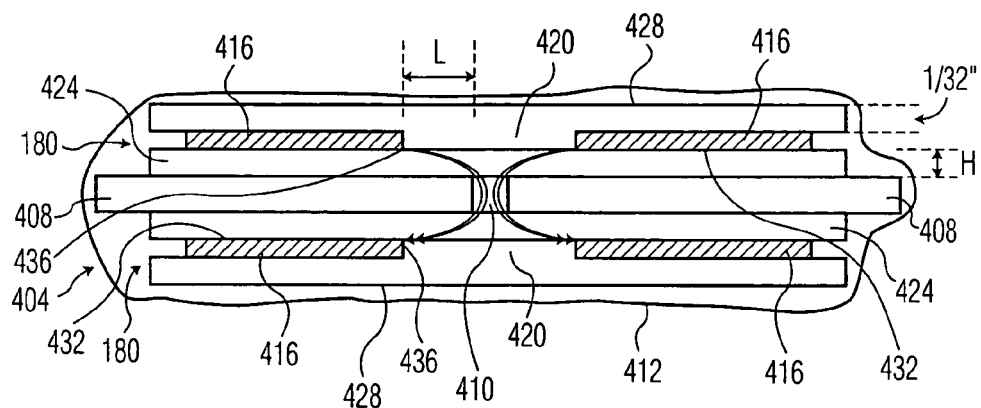
FIG. 4 is a cross-sectional view of a first embodiment of a packaged pair of pre-connected defibrillator electrode pads according to the present invention.

FIG. 4 is a cross-sectional view depicting a first embodiment for enhancing impedance variability for a packaged pair of electrodes 404 in accordance with the present invention. The packaged pair 404 includes two electrode pads 180 and an intervening electrically nonconductive element 408, preferably an electrically non-conducting, non-stick release layer such as silicon-coated paper, polyester, polypropylene, polyethylene, and/or other non-stick materials. Release layer 408 mates the two electrode pads 180 and has an opening 410. The package 412 of the packaged pair 404 surrounds the pads 180 and the release layer 408. The package 412 can be made of flexible plastic or other flexible material or may be, rigid and implemented as the electrode compartment 160 of the AED 100 for example. The electrode pad 180 has an electrode 416 which is shown to be a circular or oval shaped ring having a void or an opening 420 aligned adjacent to a release layer opening 424. Between the electrode 416 and the release layer 408 is an electrically-conductive skin-adhesive layer or medium 424, typically hydrogel, so that the electrodes 416 are mutually releasably connected by the medium. A foam or other dielectric or electrically-insulative or—nonconductive layer 428 is applied to the opposite side of the electrode 416 to shield the user from the electrode. The electrode pads 180 and the release layer 408 are preferably flexible, so that handling by the user can be detected.

In a preferred embodiment, the electrically nonconductive element 408 is disposed adjacent to the medium 424 and between the pair of electrodes 416 to act as a blocking mechanism that lengthens the electric current path. As one example, a generally flat electrode 416 may have a generally flat inner surface 432 with an edge 436, both surfaces facing each other, and an electric current path between the electrodes 416, in traveling between the respective edges 436 (shown by the arrows in FIG. 4), travels through the medium 424 laterally more than twice as far as the path travels in an electrode-to-electrode direction. In other words, the distance L in FIG. 4 is preferably at least twice as large as the distance H. As discussed in the '478 application, this distance differential creates high impedance between the electrodes 416. Manipulation of the pads, such as bending, when the user handles or removes the pads 180 from their package changes the impedance, which can be detected by the AED 100. L/H ratios of less than 2 are also contemplated for the present invention.

Since different hydrogels may have different impedances, the impedance variability may, depending upon the type of hydrogel used in the electrode pads, not change enough in reaction to a disturbance to significantly rise above the noise level as the pads are removed from their package.

Also, in order to protect users from an electric shock, those who might be inadvertently touching the electrode pads during defibrillation shock, electrodes are traditionally made with a thick layer of foam, 1/16 of an inch or greater. However, this thick foam makes the pad-to-pad construction stiffer and less sensitive to handling as they are attached to each other on opposite sides of the release layer.

In order to enhance the changes in impedance due to handling, a thinner foam layer 428 having a thickness that is no greater than 1/16 of an inch and which more preferably is around 1/32 inch, or other dielectric layer may be used as long as the dielectric properties of the new material are strong enough to withstand the defibrillation voltages. This thinner dielectric allows the pad-to-pad construction to bend a greater amount and produce larger pad-to-pad impedance changes. More generally, changing the dielectric, or replacing it with a substitute, to make the pad more flexible increases the impedance variation.

Although only one high impedance path is shown, more than one can be configured. The shape of the electrode 416 is not confined to any particular shape or to any particular number of voids 420. Correspondingly, the release layer 408 is not limited to any particular number of adjacent openings 410, as described further in the '478 application.

Figure 5:
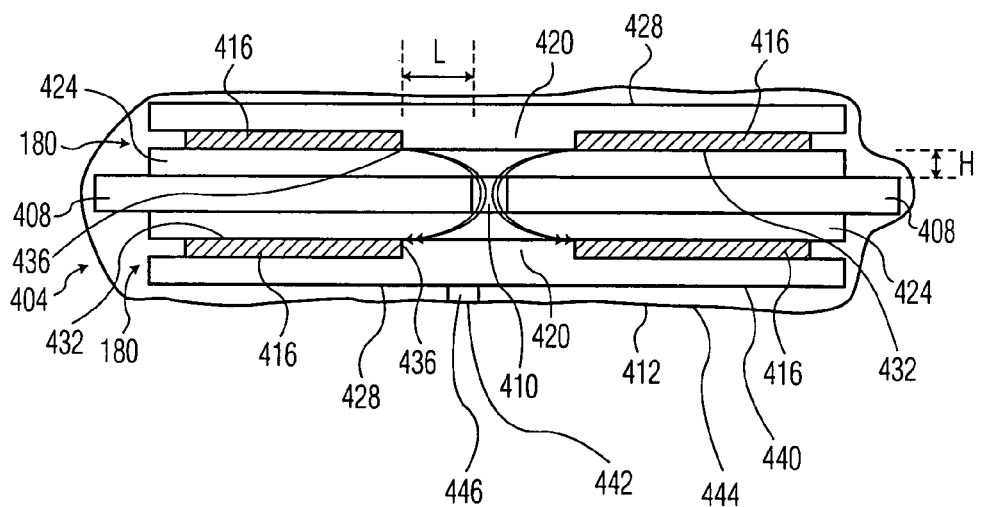
FIG. 5 is a cross-sectional view of a second embodiment of a packaged pair of pre-connected defibrillator electrode pads according to the present invention.

FIG. 5 is a cross-sectional view of a second embodiment for enhancing the impedance variability for the packaged pair of electrodes 404 in accordance with the present invention. The outer surface 440 of the foam layer 428 is joined to a portion 442 of the inside surface 444 of the package 412. The joinder can be accomplished by insertion of a piece of 2-sided tape 446. Alternatively, the adhesive swatch 446 may be hydrogel or a multi-layered film of pressure-sensitive adhesive or other substrates designed to adjust the adhesive and release properties of each side of the film. If the package 412 is rigid, e.g. the electrode compartment 160, the tape 446 is placed to adhere the bottom electrode pad 180 to the compartment.

As in the first embodiment, the hole(s) 410 in the release layer 408 allows the hydrogel from the first pad 180 to touch the hydrogel of the second pad 180, creating an electrical connection between the pads. Once this electrical connection is established, the pad-to-pad impedance can be monitored. Since the hole provides the electro/mechanical connection between pads 180, it is also the area most sensitive to mechanical disturbances, such as bending.

As the user pulls the electrodes pads 180 out of their package 412, the tape 446 keeps the bottom electrode pad 180 adhered to the package until the force becomes great enough that the electrode pad peels away. As the electrode pad is pulled, it bends in the vicinity of the release layer opening 410. This, in turn, causes a rapid, detectable change in pad-to-pad impedance. Particularly if the package, 412 is implemented as the electrode compartment 160, signal processing thresholds can optionally be set that distinguish between a minimal level of bending indicative of mere handling of the electrode pads 180 and the greater level of bending characteristic of event of removing the pads. The adhesive 436 is preferably aligned adjacent to the release layer opening 410 to render the maximum bending effect at the opening. The area of the portion 442 is preferably larger than that shown in FIG. 5 to produce more bending, but may be the same size or smaller.

Figure 6:
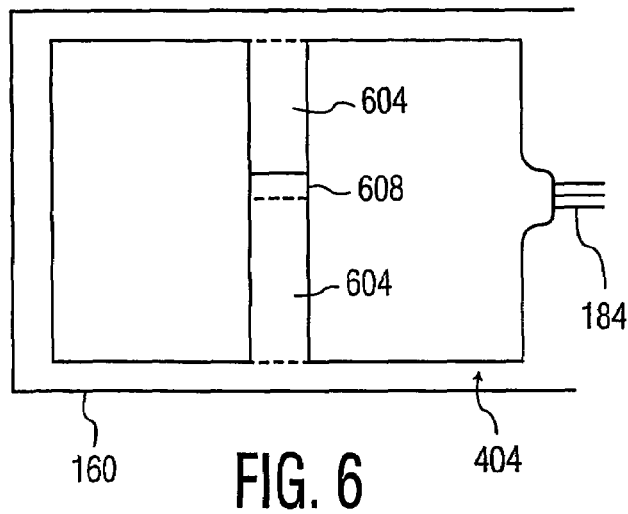
FIG. 6 is a cross-sectional view of a third embodiment of a packaged pair of pre-connected defibrillator electrode pads according to the present invention.

FIG. 6 depicts a third embodiment for enhancing impedance variability for the package pair of electrodes 404 in accordance with the present invention. A packaged electrode pad pair 404 and its accompanying lead wires 184 are held within the compartment 160 by two belts or straps 604 that mutually and adhesively attach end-to-end to surround the pair and which attach at their other ends to the compartment, which in turn surrounds the belts and the pads. The end-to-end attachment 608 is configured with an adhesive strength having a magnitude small enough to allow an operator to manually separate the belts to apply the pads 180 to a medical patient in need of defibrillation. As the user pulls the pads 180 out of their package, the straps 604, which can be made of paper, plastic, or even a thin metal foil, hold the pads and causes them to bend. The belts 604 are preferably placed around the middle of the pad pair 404, so that the bending occurs over the hole(s) 410 in the release layer 408. The area around the hole(s) 410 is the area most sensitive to impedance changes, and the large bend in this area causes a significant impedance variation that can be detected by the AED 100. As the user continues to pull the pads out of the compartment 160, the straps 604 pull apart, allowing the pads 180 to be fully removed from the compartment. Alternatively, the pads 180 may be strapped to the package 412, which may be flexible or inflexible. A further alternative implementation may employ a single, integral belt in place of the belt pair 604, so that the composition and thickness of the belt allows an operator to manually break the belt to apply the pads 180 to the medical patient in need of defibrillation.

Figure 7:
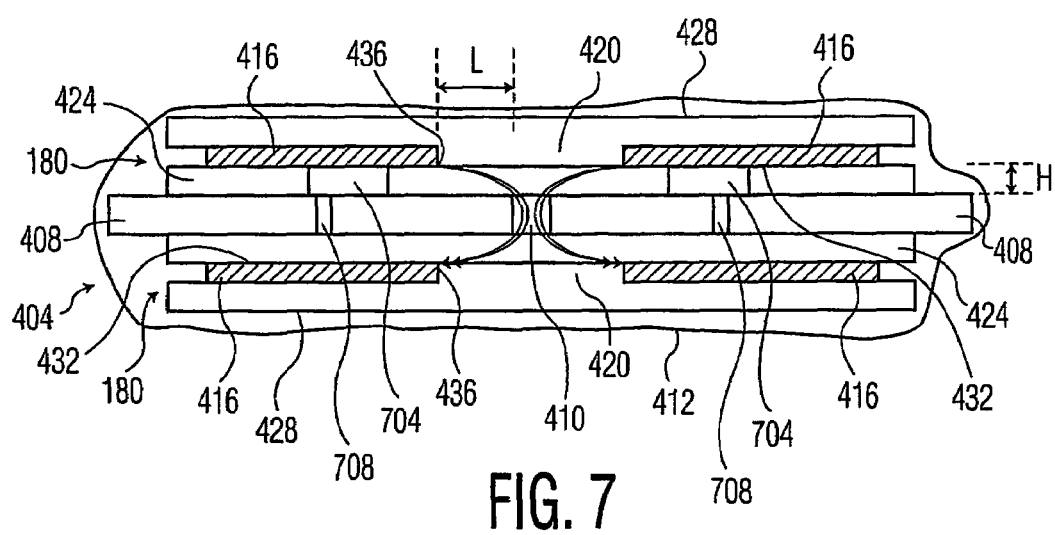
FIG. 7 is a cross-sectional view of a fourth embodiment of a packaged pair of pre-connected defibrillator electrode pads according to the present invention.

FIG. 7 portrays a fourth embodiment for enhancing impedance variability in accordance with the present invention. A small, piezoelectric substance or film sensor 704, such as a piece of metallized PVDF film, is positioned between the release layer 408 and one or both of the electrodes 416. A small hole 708 in the release layer 408 allows the back side of the PVDF film to contact the hydrogel 424 while the top side of the PVDF film touches the top electrode 416. This arrangement allows an electric current path to be created between the electrodes 416 that passes through the substance 704, the hydrogel 424 and the opening 410 in the release layer 408. More generally, the medium 424, substance 704 and layer 408 are disposed between the electrodes 416, with the substance touching at least one of the electrodes, so that movement of an electrode that deforms the substance causes an electric voltage to be generated between the electrodes. In effect, as the electrode pads 180 are pulled out of the package 160, 412, the PVDF film bends generating a voltage which is sensed by thee AED. This event or handling that causes the film to bend are detected by the AED, 100 and interpreted accordingly to mark the occurrence of handling the electrode 416 or removing of the electrode from its package.

Figure 8:
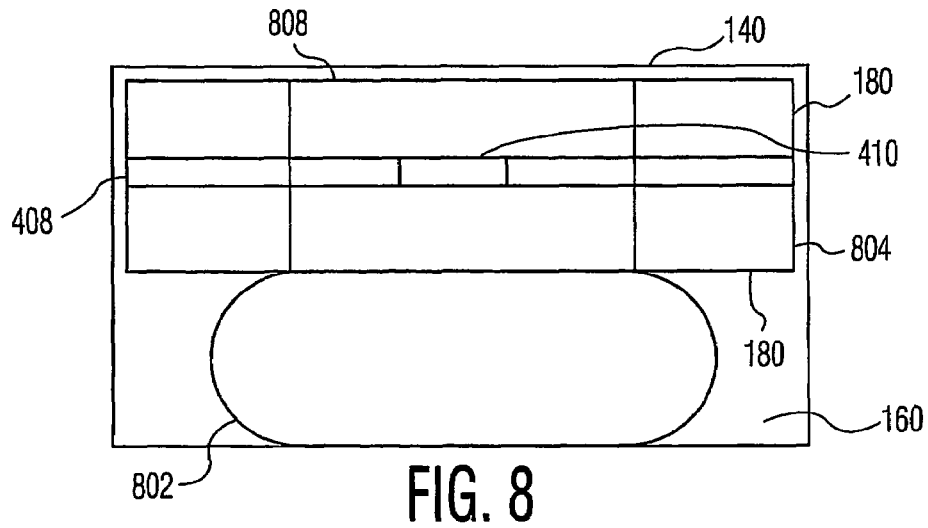
FIG. 8 is a cross-sectional view of a fifth embodiment of a packaged pair of pre-connected defibrillator electrode pads according to the present invention.

FIG. 8 depicts a fifth embodiment for enhancing impedance variability in accordance with the present invention. The pads 180 and intervening release layer 408 are fitted into a package 412, preferably the rigid compartment 160, along with an elastically compressible material such as foam rubber 802. As the package 160, 412 is sealed, the pads will be compressed upon the foam rubber 802. Preferably, the pad pair 180 and layer 408 are together generally flat, the pads having a periphery 804 and a central portion 808. The foam rubber 802 has preferably been disposed to align adjacent to the opening 410 of the pad pair 404. As the compartment lid 140 is opened, pressure by the foam rubber 802 against the central portion 808 flexes the pad pair 408. Since the opening 410 is aligned adjacent to the central portion, bending of the pad pair 404 and resulting variation in the impedance is enhanced. This embodiment works best with a sealed, rigid cartridge.

As has been demonstrated above, handling or removal of a pair of pre-connected defibrillator electrode pads from their package is detected in order to effectively time the issuance of prompts to guide the user.

It is within the intended scope of the invention that features of the various above embodiments may be combined. For example, the adhesive tape of the second embodiment and the strap of the third embodiment may be combined to cumulatively enhance the impedance variability in response to the handling or the removal of electrode pads.

While there have been shown and described what are considered to be preferred embodiments of the invention, it will, of course, be understood that various modifications and changes in form or detail could readily be made without departing from the spirit of the invention. For example, the electric circuit through the pads may be implemented with direct current (DC) or with alternating current (AC). It is therefore intended that the invention be not limited to the exact forms described and illustrated, but should be construed to cover all modifications that may fall within the scope of the appended claims.

The invention claimed is:

1. An apparatus for detecting at least one of handling of electrodes and removing of the electrodes from a package comprising:
    a pair of electrodes suitable for attachment to a patient and attached to an external defibrillator having a first prompt, each electrode including a conductor for sensing a patient electrical characteristic or delivering electricity for a defibrillation shock to a patient;
    an impedance element electrically coupled with at least one of the electrodes which varies when the associated electrode is flexed or bent;
    a current delivery circuit, coupled to the electrodes, which causes current to flow through the impedance element;
    a monitoring circuit coupled to the impedance element for monitoring a magnitude of an electrical characteristic resulting from the flow of current through the impedance element,
    wherein an occurrence of at least one of handling and removing of the electrodes is identified by the variation of the impedance of the impedance element and causes a second prompt to be generated.

2. The apparatus of claim 1, wherein the monitoring circuit includes a circuit for monitoring a magnitude of impedance, and wherein the occurrence is identified based on a variation over time in the magnitude of the impedance.

3. The apparatus of claim 2, wherein the occurrence is identified based on plural variations over time in the magnitude.

4. The apparatus of claim 1, wherein:
    the impedance element resides between the electrodes; and
    the electrodes and the impedance element are contained within a package prior to the occurrence to be identified.

5. The apparatus of claim 4, wherein the impedance element comprises an electrically-conductive hydrogel located between the electrodes.

6. A method for detecting at least one of handling of electrodes and removing of the electrodes from a package containing the electrodes, the electrodes being attached to an external defibrillator for sensing a patient electrical characteristic or delivering electricity for a defibrillation shock, the external defibrillator having a first prompt, the electrodes including an impedance element electrically coupled with at least one of the electrodes and exhibiting an impedance which varies when the impedance element is flexed or bent, the method comprising the steps of:
    monitoring a magnitude of an electrical characteristic measured from an electrical circuit having an electric current path through the impedance element;
    identifying an occurrence of at least one of handling and removing the electrodes based on variation over time in the magnitude; and
    generating a second prompt by the external defibrillator.

7. The method of claim 6, further comprising locating the electrodes in a package and electrically connecting the electrodes to the electrical circuit.

8. The method of claim 7, wherein monitoring further comprises monitoring the electrical characteristic with an electrical circuit of a defibrillator.

9. The method of claim 6, wherein monitoring further comprises monitoring the magnitude of an electrical characteristic of an electrically-conductive hydrogel of the electrodes.

10. A defibrillator apparatus comprising:
    an external defibrillator having a first prompt and an electrode pad for sensing a patient electrical characteristic or delivering electricity for a defibrillation shock which includes an impedance element electrically coupled to the electrode pad, the impedance of which changes when the electrode pad is deflected or bent;
    an integral belt surrounding the pad; and
    a monitoring circuit coupled to the electrode pad and operable to monitor the impedance of the impedance element;
    wherein a composition and a thickness of the belt causes an operator to flex or bend the pad when preparing to apply the pad to a medical patient in need of defibrillation and causes the defibrillator to generate a second prompt.

11. The defibrillator apparatus of claim 10, wherein the belt is made of at least one of paper, plastic, and metal.

12. The defibrillator apparatus of claim 11, wherein the impedance element comprises an electrically-conductive hydrogel of the electrodes.

* * * * *